United States Patent [19]

Eisner

[11] 4,243,389

[45] Jan. 6, 1981

[54] DENTAL DOWEL PIN PLACEMENT APPARATUS

[76] Inventor: Jeffrey W. Eisner, 464 W. Shenandoah, Roseburg, Oreg. 97470

[21] Appl. No.: 102,380

[22] Filed: Dec. 11, 1979

[51] Int. Cl.³ .......................................... A61C 19/00
[52] U.S. Cl. ...................................... 433/74; 433/75
[58] Field of Search ............................ 433/74, 72, 75

[56] References Cited

U.S. PATENT DOCUMENTS

| 2,836,849 | 6/1958 | Humphrey | 433/75 |
|---|---|---|---|
| 3,277,576 | 10/1966 | Kraft | 433/74 |
| 3,417,471 | 12/1968 | Mitchell | 433/72 |
| 3,553,839 | 9/1969 | Gores | 433/74 |
| 3,717,933 | 2/1973 | Charron | 433/74 |
| 3,753,291 | 8/1973 | Bocian et al. | 433/74 |
| 4,129,281 | 12/1978 | Cooper | 433/74 |

Primary Examiner—Gene Mancene
Assistant Examiner—John J. Wilson
Attorney, Agent, or Firm—James D. Givnan, Jr.

[57] ABSTRACT

A dowel pin holder having an elongate base horizontally positionable within a dental impression. A guide for installation of the base is temporarily positionable above the specific tooth impression and guides the inserted base into precise position above the tooth impression. A dowel pin holder is positionable along the elongate base as is a slidable indicator for the dowel pin holder.

6 Claims, 5 Drawing Figures

U.S. Patent
Jan. 6, 1981
4,243,389
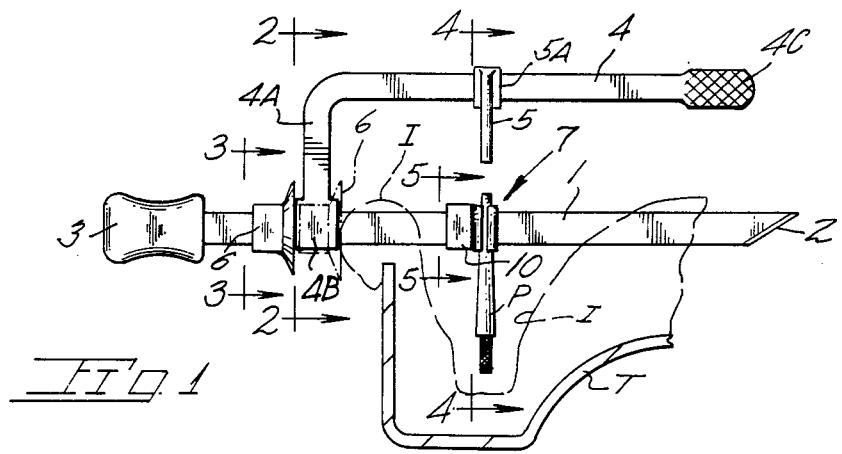
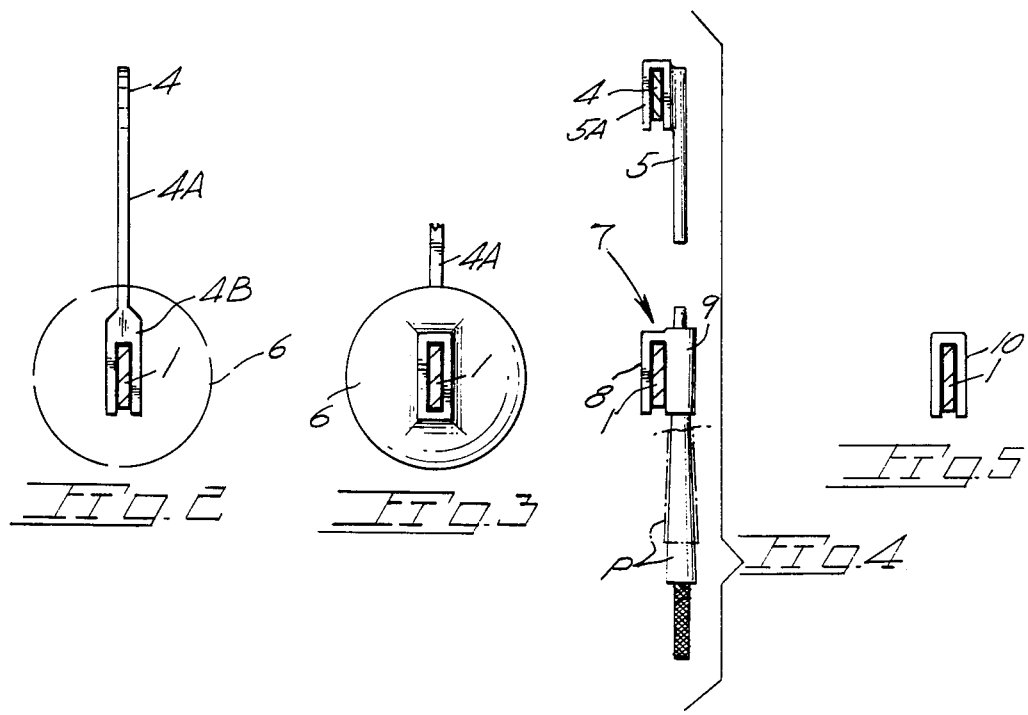

DENTAL DOWEL PIN PLACEMENT APPARATUS

BACKGROUND OF THE INVENTION

The present invention relates generally to dental devices used to position a dowel pin during the forming of a jaw reproduction.

In the making of artificial teeth, caps, crowns and other prosthetic devices, it is accepted practice to initially make a dental impression of the jaw or pertinent portion of the jaw. The impression is a negative of the jaw and teeth. A positive reproduction of the jaw and teeth is subsequently formed by the deposit of casting material in the impression which material is vibrated to enhance the quality of the reproduction. To enable removal and insertion of a tooth model from the reproduction during the manufacture and sizing of the prosthetic article, a dowel pin is positioned in the negative impression in centered relationship with the defective tooth impression whereupon a pour of casting material is made embedding the lower portion of the pin. A second pour is usually super-imposed on the first pour. Upon the material setting, the reproduction is removed from the impression and inverted whereupon a sawing operation serves to isolate the tooth model or models enabling their removal and precise repeated placement and fitting of the prosthetic device during fabrication of same. It is obvious that precise dowel pin placement in the tooth impression is necessary both for tooth model removal as well as for subsequent fitting of the prosthetic device during its manufacture.

Disclosed in the prior art are pin supporting means which attach to the impression tray or a tray supporting stand as found in U.S. Pat. Nos. 2,836,849; 3,277,576; 3,639,985 and 3,717,933. Other prior art has utilized pin supporting means which instead of attaching to the tray insertably engages the impression material as per U.S. Pat. Nos. 3,521,354 and 3,553,839.

In the known prior art it is customary to incidentally subject the dowel pin and its supporting arrangement to vibration during vibration of the plaster laden impression which not uncommonly results in dowel pin displacement. Remedying such displacement, if discernable, is often done in an imprecise manner. As earlier noted, precise dowel pin location is of prime interest for subsequent prosthetic fabrication.

SUMMARY OF THE PRESENT INVENTION

The present invention is embodied within an apparatus for horizontally inserted placement within a tray held dental impression.

A base member of the present apparatus is of elongate shape adapted for lengthwise penetration transversely through that portion of the impression above the impression of the tooth on which is to be mounted a cap or other prosthetic device. An elevated guide is temporarily positionable on the base to facilitate insertion of same directly over the concerned tooth impression.

Subsequent to taking the impression and prior to casting of the jaw reproduction, the elongate base member is guided into the moldable impression material. A dowel pin holder is set onto the base with holder location marked with a base mounted indicator. The holder with dowel pin therein are then removed. After deposit of the casting material within the impression, it is customary to subject the impression and casting material to vibration to assure a high quality, accurate jaw reproduction. A stop precludes displacement of the base during such vibration. Upon completion of the vibration, the dowel pin and its holder are reinstalled on the base in a precise manner as marked by the indicator. Accordingly, positioning of the dowel pin is done in a precise manner subsequent to vibration of the impression to thereby avoid the risk of pin displacement as encountered by those dowel pin supporting arrangements which require dowel pin placement prior to vibration of the impression.

Important objectives of the present dowel pin apparatus include the provision of an apparatus enabling both locating and supporting a dowel pin within already poured casting material ultimately constituting a jaw reproduction; the provision of a dowel pin placement apparatus providing a guide facilitating proper insertion of a base with respect to a subjacent tooth impression with the user having full view of the tooth impression facilitating accurate locator positioning and, ultimately, dowel pin positioning; the provision of a dowel pin placement apparatus permitting the dowel pin to be partially embedded within molten casting material at a desired height which may vary between different pin installations; the provision of a pin placement apparatus of uncomplicated, low cost construction which may be used in close proximity to one another in a jaw impression.

BRIEF DESCRIPTION OF THE DRAWING

In the accompanying drawing:

FIG. 1 is a front elevational view of the present apparatus on a somewhat enlarged scale;

FIGS. 2, 3, 4 and 5 are all vertical sectional views taken along lines identified by like numerals at 2—2, 3—3, 4—4, and 5—5 of FIG. 1.

DETAILED DESCRIPTION OF THE PREFERRED EMBODIMENT

With continuing attention to the drawing wherein applied reference numerals indicate parts similarly hereinafter identified, the reference numeral 1 indicates an elongate base of the present apparatus for lengthwise placement in a dental impression. The base member so positioned by the user will lie within an upright plane containing the upright axis or other desired dowel pin location of a tooth impression. The inserted end of the base member may have a pointed tip at 2 while the opposite end is provided with a fingergrip 3. A crossection of a dental impression is shown at I in phantom lines in an impression tray T.

A base guide at 4 includes a downward extension 4A terminating in an enlarged end 4B. End 4B, as best viewed in FIG. 2, is bifurcated for engagement with and removal from base 1.

In place on guide 4 is a locator at 5 which includes a bracket portion 5A. One end of guide 4 is conveniently provided with a fingergrip at 4C. To prevent displacement of base 1 during impression vibration, a stop at 6 is slidably and frictionally engageable with base 1 and is adapted to abut the exterior edge of the impression.

A dowel pin holder generally at 7 has an integrally formed bracket 8 for placement on base member 1. Holder 7 includes a split collar 9 adapted to receive different dowel pin diameters and support same at different heights relative the tooth impression to suit specific pin installations. An indicator at 10 is in abutment with holder 7.

In use, the dental impression is taken in the usual manner. The tip 2 of base member 1 is inserted into the outer portion I of the impression. Guide 4 is then set in place on base 1 and manually held over the desired base location with locator 5 positioned in axial alignment with the desired position of a later installed dowel pin whereafter base 1 is further inserted to the FIG. 1 position using superposed guide 4 to assure proper placement of base 1 (usually through an upwardly projected axis of the tooth impression). Guide 4 is thereafter removed and stop 6 slid into abutment with the impression material at I. The dowel pin and its holder and indicator 10 are positioned along the base member 1. The holder and pin are then removed with indicator 10 left in place. Casting material is subsequently deposited within the impression and subjected to vibration in the usual manner. During such vibration, base 1 is held firmly in place by the impression material and stop 6. Prior to setting of the plaster, dowel pin P, in its holder 7, is set back into place on base member 1 in abutment with indicator 10.

Upon setting of the impression deposited dental stone, all components of the present apparatus are removed leaving the partially exposed dowel pin in place. A second pour is then made with the jaw reproduction being removed from the impression after setting of the second pour. Subsequent removal of the tooth model and prosthetic fitting is all thereafter done in the conventional manner.

While I have shown and described but one embodiment of the invention it will be apparent to those skilled in the art that the invention may be embodied still otherwise without departing from the spirit and scope of the invention.

I claim:

1. An apparatus for retaining a dowel pin in partial embedment within a settable jaw reproduction cast within a dental impression, said apparatus comprising,
    an elongate base for supported engagement adjacent its ends with the impression,
    a guide for base installation carried by said base and positionable above a tooth impression,
    a dowel pin holder supported by and positionable along said base into alignment with the desired dowel pin location whereat the lower portion of the dowel pin will be subsequently embedded in the jaw reproduction, and
    indicator means positionable along said base to mark the desired location of said dowel pin holder when the latter is reinstalled on the base after impression and jaw reproduction vibration.

2. The apparatus claimed in claim 1 wherein said elongate base is adapted at its leading end for horizontal insertion into the dental impression.

3. The apparatus claimed in claim 1 wherein said guide is bifurcated for installation on and removal from said base.

4. The apparatus claimed in claim 3 additionally including a dowel pin locator carried by said guide.

5. The apparatus claimed in claim 1 wherein said dowel pin holder is expansible to receive different dowel pin diameters permitting the reception of different dowel pin sizes and alternatively a tapered dowel pin at different adjusted heights.

6. The apparatus claimed in claim 5 additionally including a stop positionable along the base to prevent base displacement during vibration of the impression and jaw reproduction therein.

* * * * *